(12) United States Patent
Bernhard

(10) Patent No.: US 6,194,629 B1
(45) Date of Patent: Feb. 27, 2001

(54) NON-SLIP BANDAGE

(76) Inventor: Mark Julian Bernhard, 44 Hillmorton Road, Rugby Warwickshire CV22 5AD (GB)

(*) Notice: Subject to any disclaimer, the term of this patent is extended or adjusted under 35 U.S.C. 154(b) by 0 days.

(21) Appl. No.: 09/214,816
(22) PCT Filed: Jul. 10, 1997
(86) PCT No.: PCT/GB97/01861
  § 371 Date: Apr. 14, 1999
  § 102(e) Date: Apr. 14, 1999
(87) PCT Pub. No.: WO98/02120
  PCT Pub. Date: Jan. 22, 1998

(30) Foreign Application Priority Data

Jul. 12, 1996 (GB) ................................... 9613785

(51) Int. Cl.$^7$ ................................... A61F 13/00
(52) U.S. Cl. ........................... 602/41; 128/882
(58) Field of Search ................ 602/41, 42, 48, 602/50, 60, 61, 74, 79; 128/882

(56) References Cited

U.S. PATENT DOCUMENTS 3,667,462 * 6/1972 Moon .
4,940,047 * 7/1990 Richter et al. .
5,856,245 * 1/1999 Caldwell et al. .

* cited by examiner

Primary Examiner—Michael A. Brown
Assistant Examiner—Lalita Hamilton

(57) ABSTRACT

In the field of bandages it is known to provide a non-slip coating to one surface of a bandage. However, previous such bandages have suffered numerous disadvantages. The disclosure relates to a bandage (1) having a resiliently stretchable, non-slip coating (3) applied to it in wavy lines extending along the length of the bandage (1). The non-slip coating is such as to provide slip resistance between the bandage (1) and the human skin, to which the bandage (1) may be applied in a compressive manner. An advantageous feature of the invention is the use of a barb hook-type fastener (5,13) the shear force which acts in a plane approximately coinciding with that of the outer surface of the bandage (1), thereby reducing the tendency of the bandage to peel apart as a result of forces arising from the compressive application of the bandage to e.g. a human limb.

36 Claims, 3 Drawing Sheets

NON-SLIP BANDAGE

The present invention relates to a novel bandage or wrap and to a novel textile material useful as a bandage or wrap.

When a limb suffers internal damage to tissue other than bone, it is common to wrap the limb in a bandage material to provide support or compression, in order to aid healing and/or to help prevent further damage. Such damage often arises in sports injuries. Some sportsmen or women bandage a limb joint for prophylactic purposes, ie. to prevent injury.

One known type of bandage is an adhesiveless elastic tube. Such a tubular bandage provides limited support and the compressive force cannot be varied. Tubular bandages are therefore of limited benefit and are not normally used, for example, by sportsmen and women.

A more effective bandage is an elasticated adhesive bandage. Such a bandage comprises an elongate strip of longitudinally semi-stretchable fabric, one major surface of which is adhesively coated. The fabric contains no elastomer or rubber. The bandage can be wrapped around a limb section as desired, in particular the compression applied and the arrangement of the bandage can be selected by the person applying the bandage, who is often a physiotherapist. An adhesive elasticated bandage therefore overcomes some of the disadvantages of a tubular bandage. Nevertheless, adhesive elasticated bandages suffer disadvantages:

(i) they are painful to remove, because they adhere to hair, (ii) they are often uncomfortable to wear and possibly restrict blood flow, (iii) they can be difficult to apply, (iv) they are not reusable, (v) they are not necessarily adjustable after use, because they are normally unusable after removal from the skin.

French Patent No. 2 609 889 discloses a bandage having undulating lines of an anti-slip material adhered to one surface thereof.

However, the stated object of the invention of French Patent No. 2 609 889 is to provide a coated bandage the coating of which does not adversely affect the elasticity of the bandage fabric, and that permits adequate ventilation of eg. skin enclosed by the bandage.

French Patent No. 2 609 889 fails to address the problem of providing a bandage having anti-slip characteristics relative to eg. human skin, that does not rely on adherence of the bandage material to the skin.

WO95/12370 discloses a bandage having regions of anti-slip material applied to at least one surface, and preferably both surfaces, of a bandage fabric.

However, the stated aim of the invention of WO95/12370 is to provide a non-slip layer that prevents slipping of overlapping bandage layers. In the preferred embodiment, the non-slip materials are applied in patterns that facilitate this effect. Again, there is no detailed disclosure of a means by which the bandage can be rendered anti-slip relative to human skin when the bandage is applied in a compressive manner.

In one aspect, the invention provides a bandage which enables the disadvantages of prior art bandages which have been appreciated by the inventor to be overcome or reduced. The bandage is as defined in Claim 1.

A bandage of the invention may be applied to a limb by placing a first end of the bandage on the limb with its slip-resistant surface facing the skin. The bandage is then wound around the limb under tension, the first end of the bandage being held in place by an at least partially overlying bandage layer. The second end of the bandage may conveniently be secured to an underlying bandage layer, suitably by means of an adhesive strip or, more preferably, by means of a tab secured to the bandage and attachable to the underlying surface by means of barbs removably engageable with material of the underlying layer. Suitable removably engageable barb/material combinations are available under the registered trade mark Velcro. Other barb/material fasteners may alternatively be used.

The elasticity (resiliency) of the bandage wrapped around the limb under tension (ie. extended from its relaxed state) causes the bandage to exert a compressive force on the limb. The applied bandage is subject to contractile forces but it does not slip against the skin, at least not to a significant extent, but because it is not stuck to the skin by adhesive, can be painlessly removed for repositioning or re-use. Unlike a tubular bandage, however, the compressive force applied by the bandage can be chosen by applying chosen tension to the bandage as it is being wrapped around the limb; similarly the arrangement of the bandage on the limb can be chosen as desired.

The bandage may in principle comprise any resiliently stretchable material. A fabric is preferred for comfort, such as a knitted fabric. The bandage is normally stretchable only in the longitudinal direction, since significant transverse stretchability detracts from the stability and support which the bandage can provide. The bandage normally is capable of a measured maximum extension of at least 50% of its relaxed length (ie. is capable of extending by at least 50% of its relaxed length) and often of at least 80%, and more desirably of 100% or more, eg. about 120%. The term "maximum extension" is discussed later in this specification.

The elastic modulus of a bandage may be expressed as the weight with which the bandage is required to be loaded to extend by 40% of the additional length of the bandage when extended from its rest state to substantially its maximum extended length. This is a standard test in the UK. Typically, a bandage of the invention has an elastic modulus of from 400 to 1300 g and more usually of from 700 to 1100 g. Preferably the modulus is between 800 and 1000 g and most preferably about 900 g.

As already stated, the bandage preferably comprises a fabric, for example a knitted fabric. Elasticity (resiliency) is suitably provided by incorporating in the knitted fabric longitudinal resilient strands, normally made of an elastomer.

A conventional fabric alone would not resist contraction of an extended (stressed) bandage wrapped around a limb. Such resistance may be provided by applying a slip-resistant material to one of the major surfaces of the bandage. The application of slip-resistant material to both sides of the bandage fabric, as proposed in WO95/12370, would reduce the usefulness of the device as a bandage, Normally the applied slip-resistant material is elastic; in any event, the anti-slip surface of the fabric is capable of broadly elastic behaviour. As suitable slip-resistant materials there may be mentioned materials having rubber-like properties, especially silicones.

Complete covering of the surface to be made slip-resistant with the slip resistant material has been found to be undesirable. Therefore, the coverage with the slip resistant material contains discontinuities. The invention includes bandages having the slip resistant material arranged in spots or patches but the slip resistant material is preferably formed as one or more generally longitudinally extending lines. There are preferably a plurality of such longitudinal lines of slip resistant material, suitably separated by a distance of between 5 and 15 mm and more preferably of between 8 and 12 mm, eg. about 10 or 11 mm. Most preferably the longitudinal lines of slip-resistant material are not straight but undulating, so that any notional straight line extending along the length of the bandage would intersect at least one line of the slip resistant material. This construction advantageously accommodates flexing of the slip-resistant material during elongation of the bandage, and also confers a desirable "power" characteristic in the sense that the forces resulting from extension of the bandage are evenly distributed, and increase at a desirable rate, across the range of extension.

In a preferred aspect, the invention provides a bandage as defined herein which comprises elongate fabric, resiliently stretchable in the longitudinal direction but substantially unstretchable in the transverse direction and having a rubber or rubber-like material applied to a major surface of the fabric. The rubber or rubber-like material is preferably a silicone. The fabric is preferably a crotchet knitted fabric having longitudinally oriented resiliently stretchable strands, eg. elastomeric strands, laid between the warp threads of the fabric.

The bandage is preferably provided at one end with a removable and reattachable fastener to fasten the end of the bandage to an underlying bandage layer when the bandage is wrapped around a limb.

Embodiments of the invention includes the use of a skin-compatible, non-adhesive slip resistant material to provide a bandage resiliently stretchable in the longitudinal direction with a slip-resistant surface, the bandage preferably being stretchable exclusively in the longitudinal direction and the slip-resistant material preferably being a silicone or other rubber. (A slip-resistant material is skin-compatible if it does not cause irritation or damage to the skin or pain in performing its function.)

The invention also provides a novel fabric, useful as a wrap or support. The fabric is a resiliently stretchable fabric having applied to a surface thereof a rubber or rubber-like material in a discontinuous arrangement. In one class of embodiments the fabric is unidirectionally stretchable and the rubber or rubber-like material is arranged in one or more continuous lines oriented generally in the stretchable direction. The fabric is preferably elongate in the stretchable direction. In a second class of embodiments, the rubber or rubber-like material is a silicone. The fabric is desirably a knitted fabric, especially a crotchet-knitted fabric; such fabric normally contains resiliently stretchable strands, usually of elastomer, arranged in the stretchable direction. The knitted fabric may be made of polyester.

The novel fabric desirably has a maximum extension and an elastic modulus as described above in relation to the bandage.

The fabric of the invention may be bandage material, that is material to be cut to length and optionally to have a fastener added, in order to form a bandage. However, the fabric is generally useful as a wrap. The invention includes the use of the fabric to form a bandage.

The present invention is further described by way of example only, with reference to the accompanying drawings, which:

Figure 1:
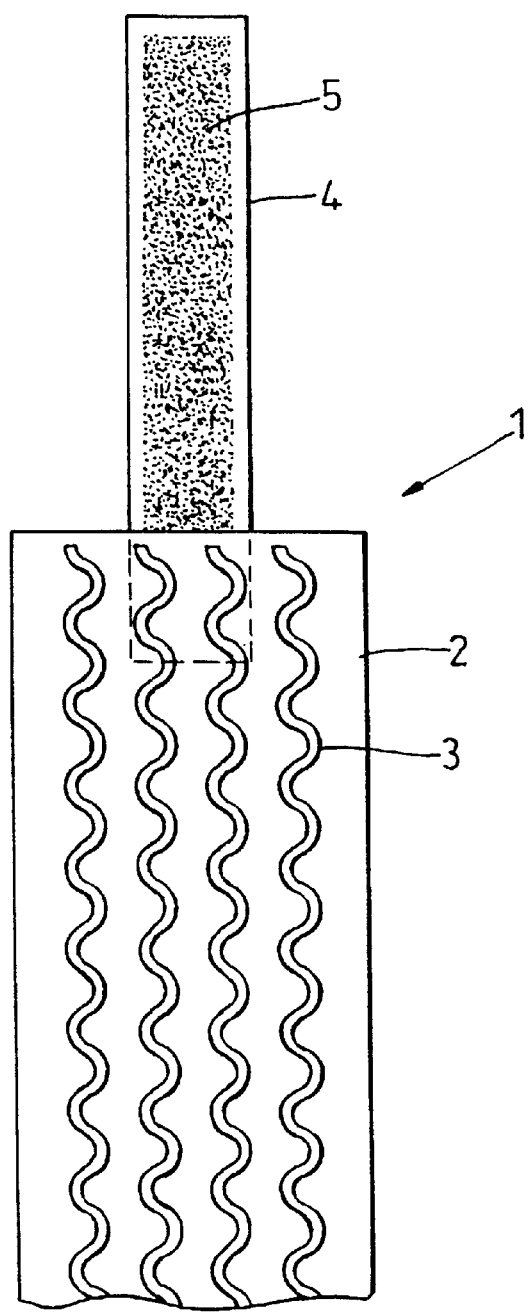
FIG. 1 is an exemplary illustration of a bandage of the invention.

FIG. 1 illustrates an end portion of a resiliently stretchable bandage or wrap 1, a surface 2 of which resists slipping when the bandage 1 is wrapped around a limb under tension. The illustrated bandage therefore has applied thereto a slip-resistant material 3. The surface 2 forms the inside surface of the bandage when wrapped around a limb and is conveniently referred to as the inside surface.

The illustrated bandage 1 is stretchable only in the longitudinal direction, ie. it resists significant transverse stretching. A transversely stretchable bandage would be unlikely to provide commercially-acceptable support but would provide some support, for which reason such less preferred bandages are not excluded from the invention.

The physical properties of the bandage are not critical, so long as, in the case of a limb support, it can function to provide support to a limb when wrapped therearound. However, we have found certain values of elastic modulus and maximum extension to be desirable, as well as the anti-slip property of a particular anti-slip coating. More particularly, the characteristics represented by a combination of such preferred values and property are especially desirable.

The bandage normally has a maximum extension of at least 50% of its relaxed length, preferably of at least 80% and more desirably of 100% or more. Usually the maximum extension is not more than 200% and is more usually not more than 150%. Most desirably the maximum extension is between 110 and 130%, eg. about 120%. By the term "maximum extension" is meant the extra length of a substantially fully stretched bandage as a percentage of the length of a fully relaxed bandage. It is common in testing textiles not to determine the true maximum extension at breaking point but to apply a standard force at which the test sample is close to its extension at breaking point, the extension at breaking point typically being within approximately 10% of the measured maximum extension. Thus, we measured maximum extension of a 3 inch (76 mm) wide bandage by applying to the free end of the bandage secured at its other end a force corresponding to that applied by a mass of 6.25 kg, 6.25 g being the load applied to 76 mm fabrics in a standard test.

As used herein, the term "elastic modulus" refers to the force required to be applied to a bandage to extend it by 40% of the extra length of the bandage when extended from a relaxed into a fully stretched state. The force is conveniently expressed as the mass which would have to be hung from the bandage to apply that force. The elastic modulus is generally at least 400 g; normally it is no more than 1300 g. More preferred minimum and maximum modulus values are 700 and 1100 g, particularly preferred maximum and minimum values being 800 and 1100 g.

The slip-resistance preferably corresponds to that provided by a silicone. Thus preferred bandages have a silicone on at least one major surface thereof and normally only one surface thereof. Room temperature vulcanising (RTV) silicone is preferred, since the uncured silicone may be applied cold to the fabric surface and allowed to cure at ambient temperature. Instead of silicone, another rubbery material may be used. The invention therefore includes a support bandage having a silicone on a surface thereof. Instead of a silicone an alternative anti-slip material may be used.

The invention also includes a method of making a fabric product or bandage, comprising applying a room temperature vulcanising silicone to a surface of a resiliently stretchable fabric.

A continuous slip-resistant surface is not necessary and, indeed, has been found to be undesirable. In preferred embodiments, the bandage therefore has a discontinuous coating of slip-resistant material 3. The invention includes bandages having the slip-resistant material 3 arranged in spots or patches but we prefer it be arranged in one or, preferably, a plurality of, lines oriented generally in a longitudinal sense. In the illustrated embodiment the lines are continuous and extend substantially the length of the bandage. The lines are preferably undulating. If there are three or more transversely spaced lines they are preferably at substantially equidistant mean spacing; the mean distance between each lateralmost line from the adjacent side edge of the fabric is preferably substantially the same as the mean spacing between the lines.

The bandage preferably comprises a fabric, and more usually a knitted fabric, especially a crotchet knitted fabric. In preferred. embodiments the yarn of the fabric is polyester yarn. Resiliency is suitably provided by longitudinal elastic (resilient) strands, preferably elastomer strands; these strands are suitably laid between the warp threads of a knitted fabric.

Thus, a preferred class of bandages comprise a fabric of crotchet knitted polyester, especially textured polyester, containing elastomer strands laid between the warp threads, one surface of the fabric having a plurality of continuous, generally longitudinal and preferably undulating lines of silicone. Preferred and most preferred characteristics of such bandages are approximately as shown in the following Table:

TABLE 1

| Characteristic | Preferred Value | Most Preferred Value |
|---|---|---|
| Width | 1–4 inches (25–100 mm) | 1 inch (76 mm) |
| Thickness | 1–3 mm | 2 mm |
| Weight per 100 m | 2–4 kg | 2.9 kg |
| Elastomer content in manufacture per 10 cm of fabric | 8–9 cm | 8.6 cm |
| Elastomer strand diameter | 1/40–1/65 inch (0.64–0.39 mm) | 1/50 inch |
| Number of elastomer strands across the bandage | 45–65 | 54 |
| Warp content (wt % of fabric) | 20–25% | 23% |
| Weft content (wt % of fabric) | 42–48% | 45% |
| Elastomer content (wt % of fabric) | 29–35% | 32% |
| Number of silicone* lines | 2–6 | 4 |
| Distance between edges of adjacent silicone lines | 5 . 15 mm | 10–11 mm |
| Separation between peaks of adjacent silicone lines | 13–23 mm | 18 mm |

*Preferably, Silicone RTV 118, a one-part, moisture-curing, translucent, self-levelling, acetoxy silicone from G E Silicones.

Normally, the bandages of said class have values for all the characteristics of the Table which are preferred or most preferred, (eg. a combination of preferred values for some characteristics and most preferred for others), but one or more characteristics may fall outside the preferred value range, is especially the width.

Reverting now to the drawing, the bandage 1 has at one end a fastener 4 for fastening the end of the bandage to an underlying layer of the bandage when it is wrapped around a limb. The fastener 4 is shown to comprise a tab, usually of fabric, extending from the end of the body of the bandage and fastenable to such an underlying bandage layer by entrapment of a plurality of minute barbs 5 on one of the tab 4 and the outside surface of the bandage in a fibrous mat on the other thereof; such "barb fasteners" are commercially available under the trade mark Velcro®. Similar fasteners sold under other names may equally readily be used. Of course, the fastening material or device (e.g. barbs or fibrous mat) need not be provided on a tab but alternatively may be provided on the body of the bandage 1. If a barb fastener is used, then the part complementary to the barbs or mat on the tab 5 or inside surface 2 of the bandage is suitably provided on the outside surface of the bandage, e.g. in a region between 4.25 inches and 6.75 inches (11 and 17 cm) from the bandage end (i.e. the end of the bandage at which the inside-facing barbs or matting are/is located) in the case of an ankle support. For example, a plurality of spaced mats may be attached to the outside surface of an ankle support bandage over such a region.

Although the fabric forming part of the inventive bandage may be manufactured in a variety of sizes, its has been found desirable for the thickness of the crocheted or knitted fabric to be no greater than 1 mm in its unstretched state. This ensures that on stretching by eg. 50% the fabric thickness decreases to approximately 0.8 mm. When stretched by 100%, the fabric thickness typically is 0.65 mm. This ensures that the bandage of the invention does not significantly increase the thickness of a limb around which it is wrapped, even in cases where there are several layers of the bandage wrapped around the limb.

Also, as illustrated by the thickness values herein, the fabric does not significantly change its thickness on stretching, thereby rendering it particularly suitable as a bandage since there it does not significantly limit a user's ability to wear clothing over the bandage.

Furthermore, the use of preferred "50s" rubber strands (ie. strands of a thickness such that 50 of them lain side by side have a width of 25.4 mm (1 inch)) to confer elasticity on the fabric, together with use of a crocheted fabric, ensures that the bandage exhibits continuous elasticity throughout the range of its extension. This in turn means that the compressive force applied by the bandage may be predictably adjusted, regardless of the degree (up to maximum extension) of extension already conferred during initial application of the bandage.

Figure 2:
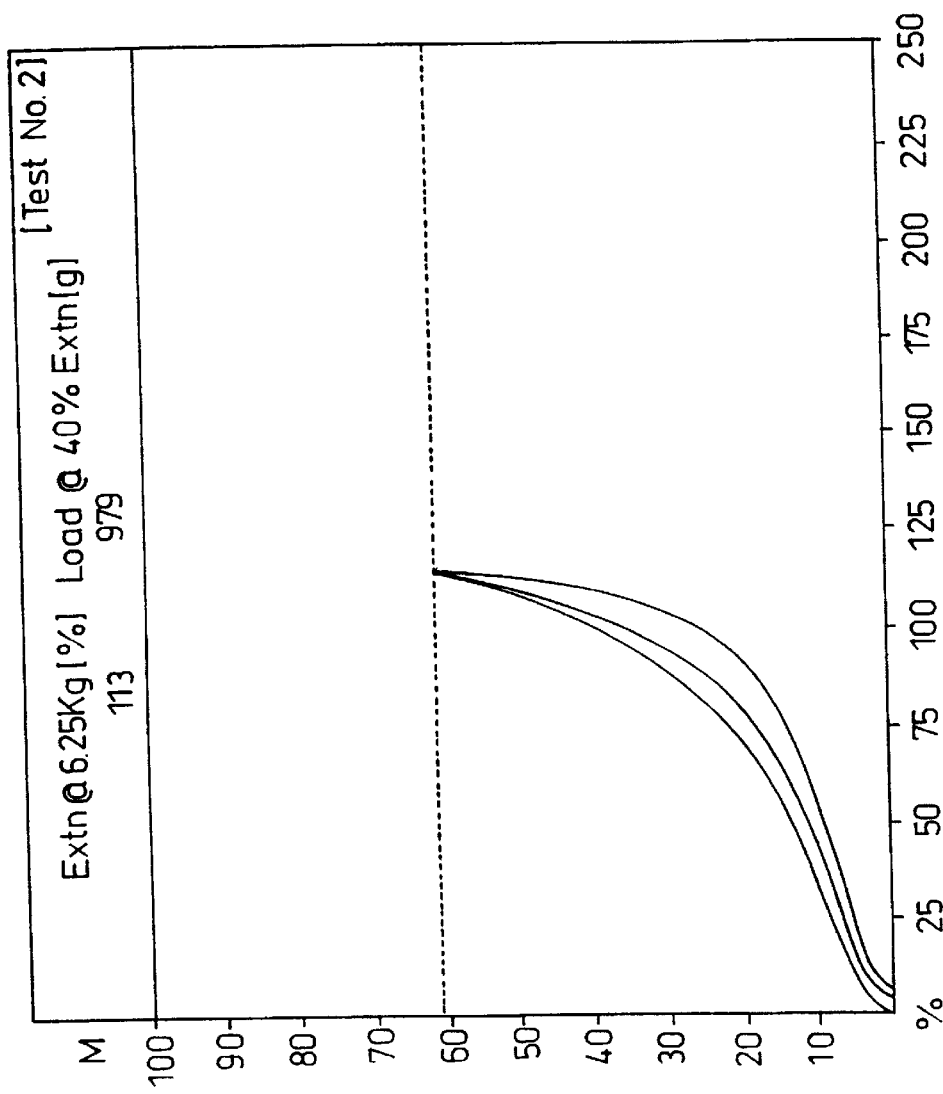
FIG. 2 is a graph showing the forces generated during extension of a bandage according to the invention.

This effect is illustrated in FIG. 2, which is a graph showing the force generated in the fabric of the bandage of the invention in N (y-axis) against percentage extension of the fabric sample (x-axis). (Details of the fabric sample tested appear in Table 2.) As is evident from FIG. 2, the fabric exhibits progressive increases in the force generated, over the entire range of extension tested (i.e. from zero extension to a maximum in the test shown of approximately 105% using a 6.25 kg test load). This means that the compressive force applied by the bandage may be finely adjusted, regardless of the extent to which the bandage has already been extended.

TABLE 2

| Quality Number | DB765 |
|---|---|
| Width | 76 mm |
| Shade | WHITE |
| Weight (grams) | 45.5 |
| Machine Number | |
| Date | 18 June 1996 |
| WITH 4 WAVY STRIPES OF SILICONE | |
| Test Report Extension/Modulus Test | |

| Extn @ 6.25 kg % | Load @ 40% Extn % |
|---|---|
| 115 | 979 |
| 113 | 979 |
| 114 | 979 |

TABLE 2-continued

| Mean Std. Day. | 114 | 979 |
|---|---|---|
| | 1 | 0 |

Another weight of the rubber strands that may be suitable for use in the fabric of the bandage of the invention is "65s", ie. strands of a thickness such that 65 of them lain side by side have a width of 25.4 mm (1 inch).

Figure 3:
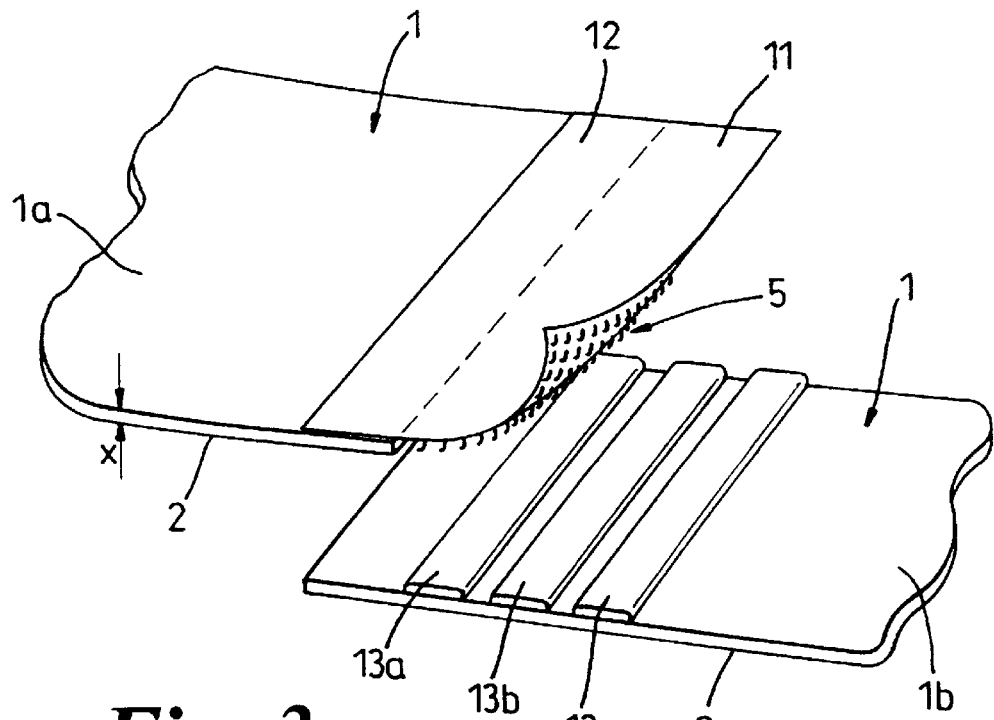
FIG. 3 shows in perspective view, a variant on the FIG. 1 embodiment.

Referring now to FIG. 3, there is shown an alternative means of attaching the barbed portion of the barb fastener referred to hereinabove.

In FIG. 3, the barbs 5 are secured to and extend inwardly from a fabric portion 11 that is in turn secured to or integral with the fabric of the bandage.

The region of the barbs 5 at the boundary of the bandage fabric 1 having the anti-slip material applied thereto, so that the barbs 5 project from substantially the same plane as the outer surface of the bandage fabric having the anti-slip material applied thereto, so that the bond between the barbs and the fibrous mat is generally coplanar with approximately the mid-point of the fabric portion 1a in FIG. 2. This construction may be achieved through forming or attachment of the barbs 5 on approximately half of one surface of a strip of fabric, the barb free part 12 of which is secured to the bandage fabric in the manier of a lap joint. The lap joint may be secured eg. by stitching, radio frequency (or other) welding or through use of adhesive materials acting between fabric 1 and portion 12.

Thus any tensile forces experienced by the fabric to which the barbs are secured are generally coplanar with the bandage fabric. This eliminates almost entirely the tendency that would otherwise occur for the free end of the fabric strip 11 supporting the barbs 5 to lift when placed in tension (eg. by virtue of compressive wrapping of the bandage of the invention about a limb). Such lifting is strongly undesirable since it tends to cause peeling of the barbs 5 from the fibrous mat secured to the bandage, with the result that the fastener may become undone or may protrude from the bandage, causing discomfort.

In other words, the positioning of the barbs and fibrous mat creates a bond that has powerful shear characteristics combined with minimal lift characteristics and eliminates to a great extent the lift characteristics normally to be experienced by the hook and loop fasteners.

Figure 4:
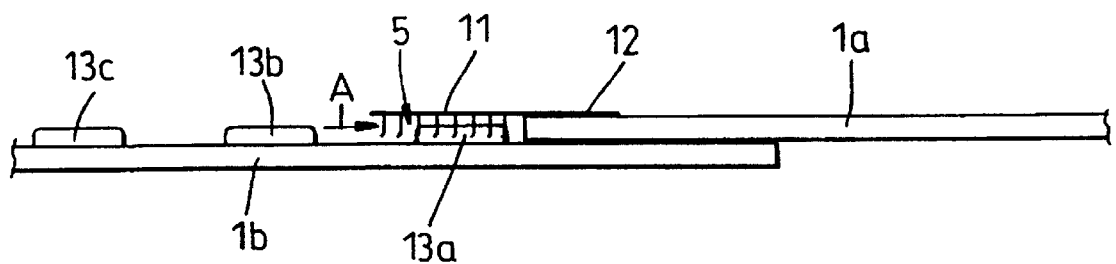
FIG. 4 is a side elevational view of the FIG. 3 embodiment.

The resulting bond is shown more clearly in FIG. 4, which shows the fastening of FIG. 2 in its closed condition. The shear forces tend to act in the plane signified by arrow A.

As is shown in FIGS. 3 and 4, the fibrous matting of the hook/loop fastener may be applied to the outer surface of the portion 1b of bandage fabric 1 in parallel bands 13a, 13b, 13c, thereby giving a range of securing positions of the barb fastener, by means of which the compressive force applied by the bandage of the invention may be adjusted.

It is not essential that the bandage have an integral fastener. For example, the free end of a bandage wrapped around a limb could be secured to an underlying bandage layer by a length of adhesive tape; if necessary fresh adhesive tape could be used when the bandage was re-arranged or re-used.

The illustrated bandage is very supportive, comfortable to wear, easy to use and re-usable as well as unlikely to restrict blood flow.

The invention includes not only a bandage or wrap as described above but also a resiliently stretchable or elastic fabric having applied thereto a rubber or rubber-like material in a discontinuous arrangement. Preferred features of the fabric are described above in relation to the bandage.

What is claimed is:

1. A resiliently stretchable bandage having a non-adhesive surface which resists slipping when the bandage is wrapped around a limb under tension, the bandage including one or more areas of slip resistant material and one or more areas lacking slip resistant material, the maximum extension of the bandage being up to 200% of its relaxed length, and the bandage having an elastic modulus of at least 400 g, the elastic modulus being expressed as the mass which would have to be hung from the bandage to extend it by 40% of the additional length of the bandage when extended from its relaxed state to substantially its maximum extended length, wherein the slip resistant material is slip resistant relative to human skin, and wherein the resilient stretchability of the bandage, the modulus and the areas of slip resistant material permit the location and magnitude of the compressive force resulting from such wrapping to be freely varied.

2. A bandage of claim 1 which is capable of extending by at least 50% of its relaxed length.

3. A bandage of claim 1 which is capable of extending by at least 80% of its relaxed length.

4. A bandage of claim 1 which is capable of extending by at least 100% of its relaxed length.

5. A bandage of any of claim 1 which, when extended to a maximum, is no more than 150% longer than when in its relaxed state.

6. A bandage of claim 1 which, when extended to a maximum, is between 110 and 130% longer than when in its relaxed state.

7. A bandage of claim 1, wherein the modulus is at least 700 g.

8. A bandage of claim 1, wherein the modulus is at least 800 g.

9. A bandage of claim 1, wherein the modulus is no more than 1300 g.

10. A bandage of claim 1, wherein the modulus is no more than 1100 g.

11. A bandage of claim 1, wherein the modulus is no more than 1000 g.

12. A bandage of claim 1, wherein the modulus is about 900 g.

13. A bandage of any of claims 1 to 12 which is stretchable in a longitudinal direction but substantially unstretchable in a transverse direction.

14. A bandage of claim 13, wherein the fabric is a polyester fabric.

15. A bandage of claim 13, wherein the fabric contains longitudinally oriented resiliently stretchable strands.

16. A bandage of claim 13, wherein the fabric contains longitudinally oriented resiliently stretchable strands.

17. A bandage of claim 16, wherein the strands are laid between the warp threads of the fabric.

18. The bandage of claim 16, wherein the stretchable strands are elastomer strands.

19. A bandage of claim 1, wherein the strands are laid between the warp threads of the fabric.

20. A bandage of claim 19, wherein the rubber or rubber-like material is a silicone.

21. A bandage of claim 19, wherein the slipresitrant surface has a discontinuous coverage of said material.

22. A bandage of claim 21, wherein said material is formed as one or more generally longitudinal lines.

23. A bandage of claim 22 wherein, the line or lines undulate(s).

24. The bandage of claim 22, wherein there are a plurality of lines, spaced apart transversely.

25. A bandage of claim 24, wherein the lines are separated by a distance of from 5 to 15 mm.

26. The bandage of claim 25, wherein the lines are separated by the distance of from 8 to 12 mm.

27. A bandage of claim 1, which is provided at one end of a reusable fastener to fasten the end of the bandage to an underlying bandage layer when the bandage is wrapped around a limb.

28. A bandage of any of claims 1 wherein the thickness of the fabric lies in the range 0.89–1.7 mm when in unstretched state.

29. A bandage according to claim 1 wherein the thickness of the fabric lies in the range 0.5 mm–0.9 mm when in its fully streched state.

30. A bandage according to claim 1, including a barb-type fastener the barbs of which are secured on a piece of fabric having a barb-free portion secured to the fabric of the bandage so that the barbs project from a plane substantially coplanar with the outer surface of the bandage.

31. A bandage according to claim 30 wherein the barb-free portion is secured to the bandage fabric by welding.

32. A bandage according to claim 30 wherein the barb-free portion is secured to the bandage fabric by stitching.

33. A bandage according to claim 30, wherein the barb-free portion is secured to the bandage fabric by means of an adhesive compound.

34. A bandage according to claim 1 that is continuously elastic over its intire range of extension.

35. An elongate fabric bandage according to claim 1 which is resiliently stretchable in a longitudinal direction but substanlially unstrechable in a tranverse direction and has a rubber or rubber-like material applied to a major surface of the fabric.

36. A bandage of claim 35, the major surface of which has a discontinous covering of said material.

* * * * *